(12) United States Patent
Groninger et al.

(10) Patent No.: US 9,465,008 B2
(45) Date of Patent: Oct. 11, 2016

(54) METHOD AND SYSTEM FOR EDDY CURRENT DEVICE DYNAMIC GAIN ADJUSTMENT

(71) Applicant: General Electric Company, Schenectady, NY (US)

(72) Inventors: Daniel Scott Groninger, Port Royal, PA (US); Soundarrajan Kaliaperumal, Karnataka (IN); Galen Lee Swyers, Yeagertown, PA (US); David George Perrett, Flintshire (GB)

(73) Assignee: General Electric Company, Schenectady, NY (US)

( * ) Notice: Subject to any disclaimer, the term of this patent is extended or adjusted under 35 U.S.C. 154(b) by 154 days.

(21) Appl. No.: 14/304,180

(22) Filed: Jun. 13, 2014

(65) Prior Publication Data

US 2015/0362462 A1 Dec. 17, 2015

(51) Int. Cl.
*G01N 27/90* (2006.01)
*G01B 7/06* (2006.01)

(52) U.S. Cl.
CPC ........... *G01N 27/9086* (2013.01); *G01B 7/105* (2013.01); *G01N 27/9046* (2013.01)

(58) Field of Classification Search
CPC ........ G01N 27/90; G01N 27/82; G01B 7/06; G01B 7/105
See application file for complete search history.

(56) References Cited

U.S. PATENT DOCUMENTS

| | | | |
|---|---|---|---|
| 3,345,563 A | 10/1967 | Wood | |
| 3,611,120 A | 10/1971 | Forster | |
| 3,679,968 A | 7/1972 | Commercon et al. | |
| 4,564,809 A | 1/1986 | Hueschelrath et al. | |
| 4,609,870 A | 9/1986 | Lale et al. | |
| 6,798,197 B2 | 9/2004 | Lopez | |
| 6,809,671 B1 | 10/2004 | Lopez | |
| 7,494,929 B2 | 2/2009 | Swedek et al. | |
| 7,560,920 B1 * | 7/2009 | Ouyang | G01N 27/902 324/240 |
| 7,670,206 B2 | 3/2010 | Togawa et al. | |
| 7,854,646 B2 | 12/2010 | Togawa et al. | |

(Continued)

FOREIGN PATENT DOCUMENTS

| | | |
|---|---|---|
| EP | 0068503 B1 | 3/1987 |
| GB | 2095842 A | 10/1982 |

OTHER PUBLICATIONS

International Search Report and Written Opinion, dated Jul. 17, 2015, for co-pending International application No. PCT/US2015/030934 (10 pgs).

*Primary Examiner* — Tung X Nguyen
*Assistant Examiner* — Zannatul Ferdous
(74) *Attorney, Agent, or Firm* — Armstrong Teasdale LLP

(57) ABSTRACT

A method and system for dynamically adjusting a gain of an eddy current device are provided. The method includes providing calibration information to the eddy current device using a probe and switching between a first mode and a second mode of the eddy current device, the first mode exciting only a first coil to measure liftoff of the probe from a surface of a workpiece, the second mode exciting the first coil and a second coil to measure dimensions of a flaw within a workpiece. The method also includes determining a thickness of a non-conductive coating covering at least a portion of the workpiece using the first coil, adjusting a gain setting of the eddy current device based on the determined thickness and the calibration information, and determining dimensions of the flaw using the first and second coils and the adjusted gain setting.

20 Claims, 3 Drawing Sheets

(56) References Cited

U.S. PATENT DOCUMENTS

| | | | |
|---|---|---|---|
| 8,013,600 B1* | 9/2011 | Yepez, III | G01N 27/9033 324/240 |
| 8,187,977 B2 | 5/2012 | Swedek et al. | |
| 8,408,965 B2 | 4/2013 | Bennett et al. | |
| 2010/0099334 A1 | 4/2010 | Bennett et al. | |
| 2012/0227903 A1 | 9/2012 | Swedek et al. | |
| 2013/0132012 A1* | 5/2013 | Tian | G01B 7/105 702/65 |
| 2013/0193960 A1* | 8/2013 | Nishimizu | G01N 27/9006 324/240 |
| 2013/0249540 A1 | 9/2013 | Lepage | |

* cited by examiner

METHOD AND SYSTEM FOR EDDY CURRENT DEVICE DYNAMIC GAIN ADJUSTMENT

BACKGROUND

This description relates to component inspection, and, more particularly, to a method and system for dynamically adjusting eddy current device gain to compensate for varying component coating thickness.

In eddy current flaw detection, a problem that is frequently encountered during eddy current inspection is coatings (paint or other material) that varies in thickness covering the conductive part under test. The variable thickness of the coating causes the coil of the eddy current probe to vary in distance from the test material, causing variations in the response seen from a flaw of identical dimensions.

BRIEF DESCRIPTION

In one embodiment, a computer-implemented method for dynamically adjusting a gain of an eddy current device, the eddy current device communicatively coupled to a probe having at least a first coil and a second coil, the method implemented using a computer-controlled eddy current device coupled to a user interface and a memory device wherein the method includes providing calibration information to the eddy current device using the probe and switching between a first mode and a second mode of the eddy current device, the first mode exciting only the first coil to measure liftoff of the probe from a surface of a workpiece, the second mode exciting the first and second coils to measure dimensions of a flaw within the workpiece. The method also includes determining a thickness of a non-conductive coating covering at least a portion of the workpiece using the first coil, adjusting a gain setting of the eddy current device based on the determined thickness and the calibration information, and determining dimensions of the flaw using the first and second coils and the adjusted gain setting.

In another embodiment, an eddy current measuring system includes a processor coupled to a user interface and a memory device. The processor is programmed to generate a plurality of multi-plexed eddy current probe excitation currents. The eddy current measuring system further includes a probe including at least a first coil and a second coil and configured to receive the excitation currents. The eddy current measuring system also includes a dynamic gain adjustment circuit configured alternately to determine a gain signal relative to a thickness of a coating in contact with the probe using the first coil and to apply the gain signal to an output signal of the first and second coils.

In yet another embodiment, one or more non-transitory computer-readable storage media include computer-executable instructions embodied thereon, which when executed by at least one processor of an eddy current device, the computer-executable instructions cause the at least one processor to receive calibration information using an eddy current probe communicatively coupled to the at least one processor, switch between a first mode and a second mode of the eddy current device, the first mode exciting only a first coil of the eddy current probe to measure liftoff of the eddy current probe from a surface of a workpiece, the second mode exciting the first coil and a second coil to measure dimensions of a flaw within the workpiece, determine a thickness of a non-conductive coating covering at least a portion of the workpiece using the first coil, adjusting a gain setting of the eddy current device based on the determined thickness and the calibration information, and determine dimensions of the flaw using the first and second coils and the adjusted gain setting.

BRIEF DESCRIPTION OF THE DRAWINGS

FIG. 1 is a schematic block diagram of an eddy current measuring system in accordance with an example embodiment of the present disclosure.

FIG. 2 is a schematic block diagram of example computing devices and that may be used in the eddy current measuring system shown in FIG. 1.

FIG. 3 is a flow diagram of a computer-implemented method for dynamically adjusting a gain of an eddy current device in accordance with an example embodiment of the present disclosure.

Although specific features of various embodiments may be shown in some drawings and not in others, this is for convenience only. Any feature of any drawing may be referenced and/or claimed in combination with any feature of any other drawing.

Unless otherwise indicated, the drawings provided herein are meant to illustrate features of embodiments of the disclosure. These features are believed to be applicable in a wide variety of systems comprising one or more embodiments of the disclosure. As such, the drawings are not meant to include all conventional features known by those of ordinary skill in the art to be required for the practice of the embodiments disclosed herein.

DETAILED DESCRIPTION

The following detailed description illustrates embodiments of the disclosure by way of example and not by way of limitation. It is contemplated that the disclosure has general application to analytical and methodical embodiments of multiplexing a calibration monitoring channel and a measuring channel to provide dynamic gain adjustments for changing conditions during a series of measurements in industrial, commercial, and residential applications.

Embodiments of this disclosure make use of an instrument and probe combination that can be operated in several modes sequentially, one of which provides a method for measuring coating thickness and another mode that is better at locating material flaws. A calibration process measures the same flaws with shims of varying thickness and develops a transfer function to adjust gain on a flaw detection channel based on the coating thickness.

The following description refers to the accompanying drawings, in which, in the absence of a contrary representation, the same numbers in different drawings represent similar elements.

Figure 1:
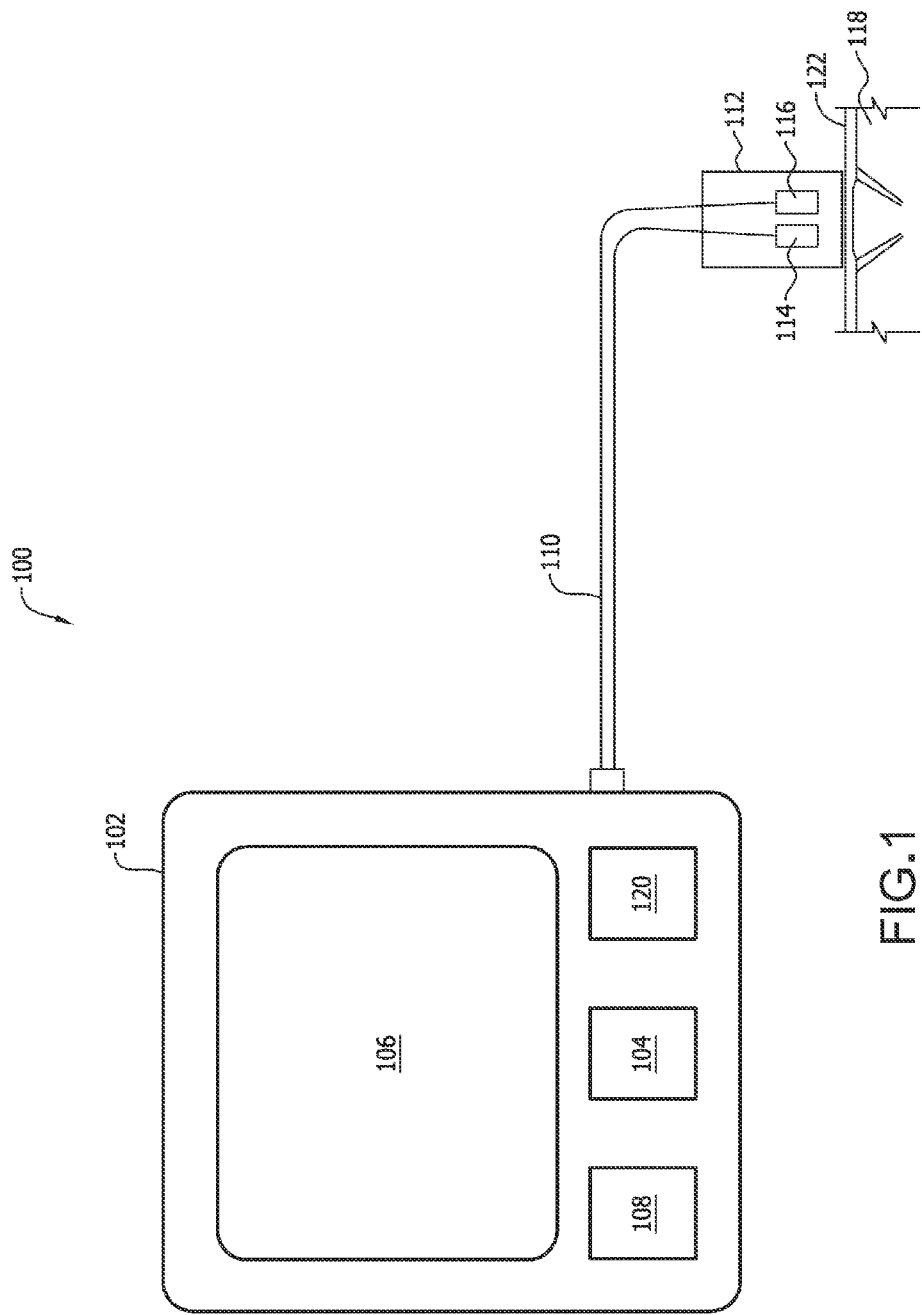
FIGS. 1-3 show example embodiments of the method and apparatus described herein.

FIG. 1 is a schematic block diagram of an eddy current measuring system 100 in accordance with an example embodiment of the present disclosure. In the example embodiment, an eddy current device 102 includes a processor 104 is communicatively coupled to a user interface 106 and a memory device 108. In various embodiments, processor 104 is programmed to generate multi-plexed eddy current probe excitation currents, which are transmitted through a conduit 110 to a probe 112. Probe 112 includes at least a first coil 114 and a second coil 116. Coils 114 and 116 are configured to receive the excitation currents and use the excitation currents to generate an expanding and collapsing magnetic field in and around a respective one of coils 114 and 116. Coils 114 and 116 are configured to operate individually and independently with respect to each other as, for example, an absolute probe. Coils 114 and 116 are also configured to operate cooperatively as, for example, a differential probe. In the example embodiment, coils 114 and 116 are wound oppositely with respect to each other, although coils 114 and 116 could also be wound additively.

When operated as an absolute probe in a first mode of eddy current measuring system 100, probe 112 uses a single one of coils 114 and 116 to generate eddy currents in a workpiece 118 and sense changes in a magnetic field produced by an interaction of the magnetic field generated by coils 114 or 116 and the field generated by the eddy currents. An alternating current (AC) is passed through the coil, which generates the expanding and collapsing magnetic field in and around the coil. When probe 112 is positioned proximate workpiece 118, the changing magnetic field generates eddy currents within the material. The generation of the eddy currents uses energy from the coil, which appears as an increase in the electrical resistance of the coil. The eddy currents generate their own magnetic field, which opposes the magnetic field of the coil and changes the inductive reactance of the coil. By measuring the absolute change in impedance of the coil, information, such as, dimension, orientation, and location information can be gained about workpiece 118. In the example embodiment, when operating in the absolute mode, coils 114 or 116 are used for liftoff measurements, however they can also be used for used for flaw detection, conductivity measurements, and thickness measurements in other modes.

When operated as a differential probe in a second mode of eddy current measuring system 100, and coils 114 and 116 are positioned over a flaw-free area of workpiece 118 or over a test block in an area devoid of flaws, no differential signal is developed between coils 114 and 116 because they are both inspecting identical material. However, when one coil is over a defect and the other is over good material, a differential signal is produced. In differential mode coils 114 and 116 are very sensitive to defects yet relatively insensitive to slowly varying properties such as gradual dimensional or temperature variations. Probe wobble signals are also reduced with coils 114 and 116 operating in differential mode.

Eddy current measuring system 100 also includes a dynamic gain adjustment circuit 120 configured alternately to determine a gain signal relative to a thickness of a coating in contact with the probe using first coil 114 and to apply the gain signal to an output signal of coils 114 and 116 operating in a differential second mode of eddy current measuring system 100. Processor 104 is configured to switch the eddy current measuring system between the first mode and second mode of the eddy current device at a rate selectable by a user. In the first mode only first coil 114 is operated in an absolute probe mode. The gain is determined based on measurements made during the first mode. Processor 104 then switches eddy current measuring system 100 to the second mode, where the gain is applied to an output of coils 114 and 116 operating in a differential probe mode. In an embodiment, processor 104 is configured to switch eddy current measuring system 100 between the first mode and the second mode at a rate greater than one-tenth Hertz (Hz). In other embodiments, processor 104 is configured to switch eddy current measuring system 100 between the first mode and the second mode at a rate greater than one thousand Hertz (Hz). In still other embodiments, processor 104 is configured to switch eddy current measuring system 100 between the first mode and the second mode at a rate greater than fifty thousand Hertz (Hz)

To facilitate generating the gain signal, readings of a known test specimen (not shown) are taken using probe 112 during a calibration mode of eddy current measuring system 100. The known test specimen includes a simulated flaw of known dimensions, orientation, and position (i.e., depth below a surface of the test specimen. A plurality of nonconductive coating simulators are used to vary a thickness of a coating over the test specimen. Readings of the test specimen and a selected set of the coating simulators are associated with gain ranges, which can be stored in, for example, memory device 108 or dynamic gain circuit 120. Moreover, the readings can be reduced to a formula of terms and constants and stored in, for example, memory device 108 or dynamic gain circuit 120.

Figure 2:
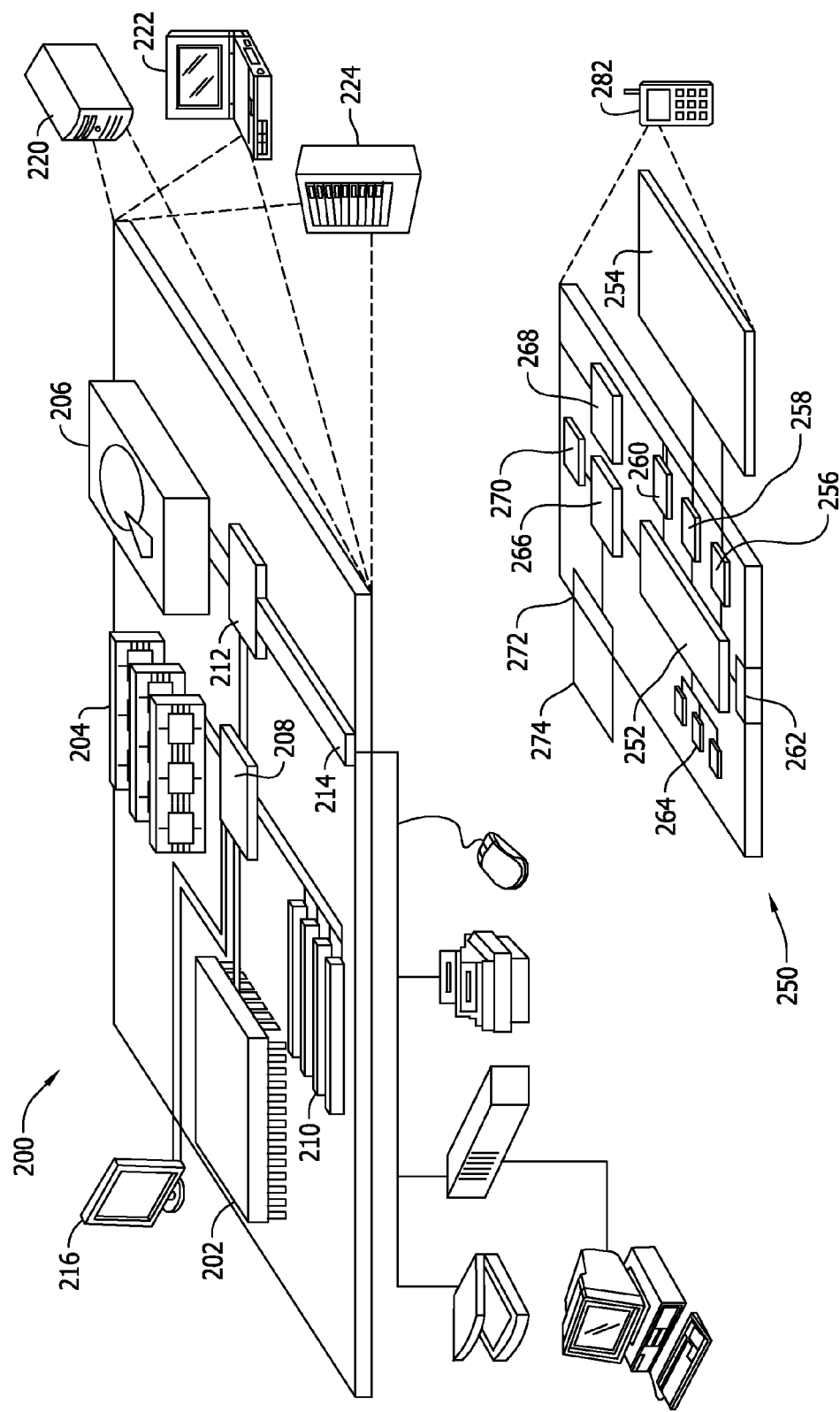

FIG. 2 is a schematic block diagram of example computing devices 200 and 250 that may be used in eddy current measuring system 100 shown in FIG. 1. More specifically, FIG. 2 shows an example of a computing device 200 and a mobile computing device 250, which may be used with the techniques described here. Computing device 200 is intended to represent various forms of digital computers, such as laptops, desktops, workstations, personal digital assistants, servers, blade servers, mainframes, tablets, phablets, and other appropriate computers. Computing device 250 is intended to represent various forms of mobile devices, such as personal digital assistants, cellular telephones, smart phones, and other similar computing devices. The components shown here, their connections and relationships, and their functions, are meant to be examples only, and are not meant to limit implementations of the disclosures described and/or claimed herein.

Computing device 200 includes a processor 202, a memory 204, a storage device 206, a high-speed interface/controller 208 connecting to memory 204 and high-speed expansion ports 210, and a low speed interface/controller 212 connecting to a low speed bus 214 and storage device 206. Each of the components 202, 204, 206, 208, 210, and 212, are interconnected using various buses, and may be mounted on a common motherboard or in other manners as appropriate. The processor 202 can process instructions for execution within the computing device 200, including instructions stored in the memory 204 or on the storage device 206 to display graphical information for a GUI on an external input/output device, such as display 216 coupled to high-speed interface/controller 208. In other implementations, multiple processors and/or multiple buses may be used, as appropriate, along with multiple memories and types of memory.

The memory 204 stores information within the computing device 200. In one implementation, the memory 204 is a volatile memory unit or units. In another implementation, the memory 204 is a non-volatile memory unit or units. The memory 204 may also be another form of computer-readable medium, such as a magnetic or optical disk.

The storage device 206 is capable of providing mass storage for the computing device 200. In one implementation, the storage device 206 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 204, the storage device 206, or memory on processor 202.

High-speed interface/controller 208 manages bandwidth-intensive operations for the computing device 200, while the low speed interface/controller 212 manages lower bandwidth-intensive operations. Such allocation of functions is example only. In one implementation, high-speed interface/controller 208 is coupled to memory 204, display 216 (e.g., through a graphics processor or accelerator), and to high-speed expansion ports 210, which may accept various expansion cards (not shown). In the implementation, low-speed interface/controller 212 is coupled to storage device 206 and low-speed bus 214. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 200 may be implemented in a number of different forms, as shown in the figure. For example, it may be implemented as a standard server 220, or multiple times in a group of such servers. It may also be implemented as part of a rack server system 224. In addition, it may be implemented in a personal computer such as a laptop computer 222. Alternatively, components from computing device 200 may be combined with other components in a mobile device (not shown), such as computing device 250. Each of such devices may contain one or more of computing device 200, 250, and an entire system may be made up of multiple computing devices 200, 250 communicating with each other.

Computing device 250 includes a processor 252, memory 264, an input/output device such as a display 254, a communication interface 266, and a transceiver 268, among other components. The computing device 250 may also be provided with a storage device, such as a microdrive or other device, to provide additional storage. Each of the components 250, 252, 264, 254, 266, and 268, are interconnected using various buses, and several of the components may be mounted on a common motherboard or in other manners as appropriate.

The processor 252 can execute instructions within the computing device 250, including instructions stored in the memory 264. The processor may be implemented as a chipset of chips that include separate and multiple analog and digital processors. The processor may provide, for example, for coordination of the other components of the computing device 250, such as control of user interfaces, applications run by computing device 250, and wireless communication by computing device 250.

Processor 252 may communicate with a user through control interface 258 and display interface 256 coupled to a display 254. The display 254 may be, for example, a TFT LCD (Thin-Film-Transistor Liquid Crystal Display) or an OLED (Organic Light Emitting Diode) display, or other appropriate display technology. The display interface 256 may comprise appropriate circuitry for driving the display 254 to present graphical and other information to a user. The control interface 258 may receive commands from a user and convert them for submission to the processor 252. In addition, an external interface 262 may be in communication with processor 252, so as to enable near area communication of computing device 250 with other devices. External interface 262 may provide, for example, for wired communication in some implementations, or for wireless communication in other implementations, and multiple interfaces may also be used.

The memory 264 stores information within the computing device 250. The memory 264 can be implemented as one or more of a computer-readable medium or media, a volatile memory unit or units, or a non-volatile memory unit or units. Expansion memory 274 may also be provided and connected to computing device 250 through expansion interface 272, which may include, for example, a SIMM (Single In Line Memory Module) card interface. Such expansion memory 274 may provide extra storage space for computing device 250, or may also store applications or other information for computing device 250. Specifically, expansion memory 274 may include instructions to carry out or supplement the processes described above, and may include secure information also. Thus, for example, expansion memory 274 may be provided as a security module for computing device 250, and may be programmed with instructions that permit secure use of computing device 250. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 264, expansion memory 274, or memory on processor 252 that may be received, for example, over transceiver 268 or external interface 262.

Computing device 250 may communicate wirelessly through communication interface 266, which may include digital signal processing circuitry where necessary. Communication interface 266 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 268. In addition, short-range communication may occur, such as using a Bluetooth, Wi-Fi, or other such transceiver (not shown). In addition, GPS (Global Positioning system) receiver module 270 may provide additional navigation- and location-related wireless data to computing device 250, which may be used as appropriate by applications running on computing device 250.

Computing device 250 may also communicate audibly using audio codec 260, which may receive spoken information from a user and convert it to usable digital information. Audio codec 260 may likewise generate audible sound for a user, such as through a speaker, e.g., in a handset of computing device 250. Such sound may include sound from voice telephone calls, may include recorded sound (e.g., voice messages, music files, etc.) and may also include sound generated by applications operating on computing device 250.

The computing device 250 may be implemented in a number of different forms, as shown in the figure. For example, it may be implemented as a smart phone 282, personal digital assistant, a computer tablet, or other similar mobile device.

Thus, various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In the example embodiment, computing devices 200 and 250 are configured to receive and/or retrieve data pertaining to the creation, review and revision of online advertisements; data regarding advertisers, advertising links or impressions corresponding to those advertisers that appear on a web page, and metrics corresponding to the appearance of those impressions on that web page, etc., from various other computing devices connected to computing devices 200 and 250 through a communication network, and store this data within at least one of memory 204, storage device 206, and memory 264. Computing devices 200 and 250 are further configured to manage and organize the data within at least one of memory 204, storage device 206, and memory 264 using the techniques described herein.

Figure 3:
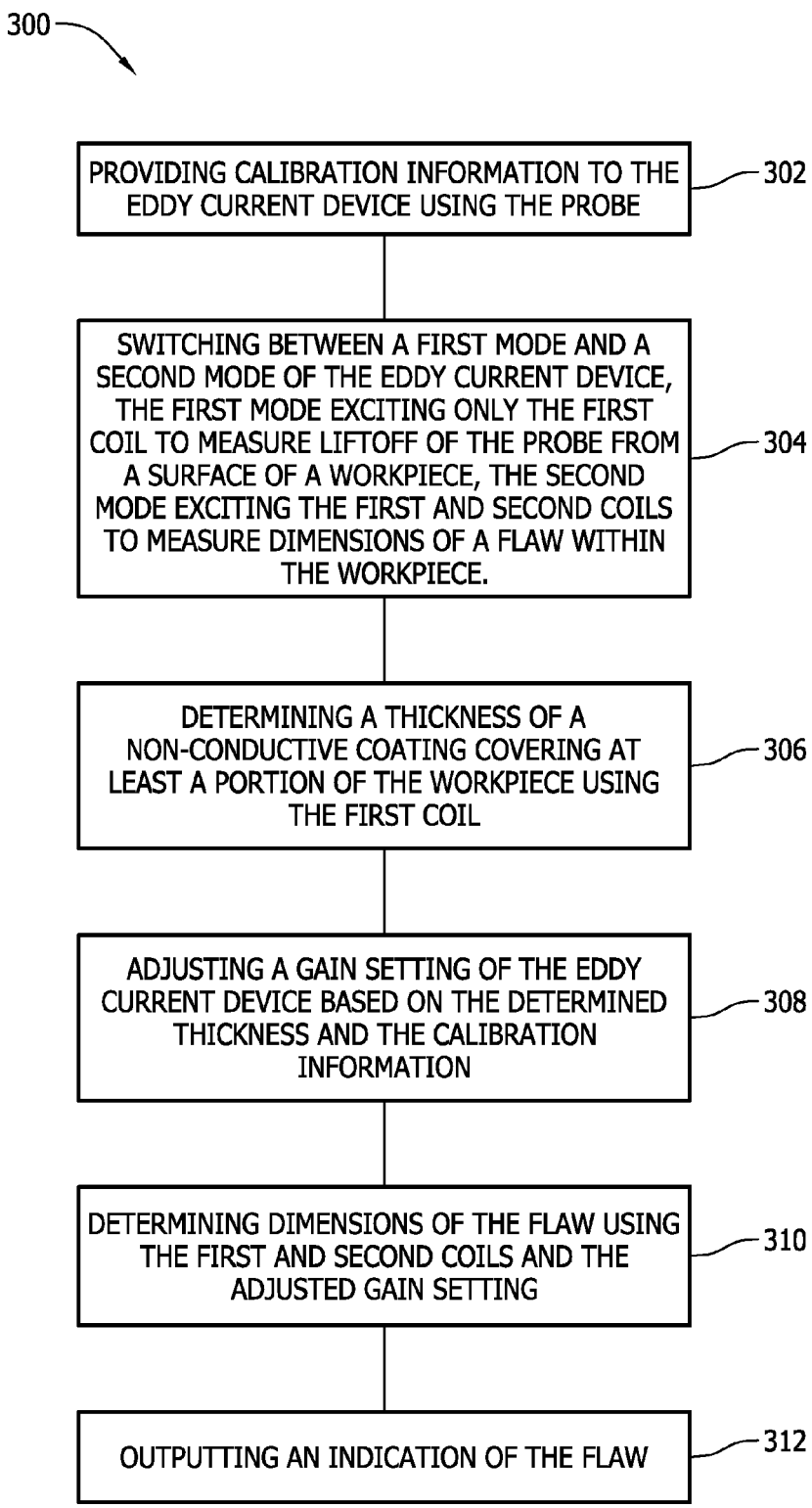

FIG. 3 is a flow diagram of a computer-implemented method 300 for dynamically adjusting a gain of an eddy current device in accordance with an example embodiment of the present disclosure. In the example embodiment, the eddy current device is communicatively coupled to a probe having at least a first coil and a second coil. Method 300 is implemented using a computer-controlled eddy current device coupled to a user interface and a memory device. Method 300 includes providing 302 calibration information to the eddy current device using the probe and switching 304 between a first mode and a second mode of the eddy current device wherein the first mode excites only the first coil to measure liftoff of the probe from a surface of a workpiece and the second mode excites the first and second coils to measure dimensions of a flaw within the workpiece. Method 300 further includes determining 306 a thickness of a non-conductive coating covering at least a portion of the workpiece using the first coil, adjusting 308 a gain setting of the eddy current device based on the determined thickness and the calibration information, determining 310 dimensions of the flaw using the first and second coils and the adjusted gain setting, and outputting 312 an indication of the flaw.

Method 300 optionally includes switching between a first mode and a second mode of the eddy current device at a frequency of greater than 0.1 Hertz (Hz). Method 300 also optionally includes switching between a first mode and a second mode of the eddy current device at a frequency of greater than 5.0 kilohertz (kHz). Method 300 further optionally includes adjusting the gain setting of the eddy current device based on the determined thickness and the calibration information by comparing a current determined thickness to a thickness range of the calibration information, selecting a gain value of the calibration information corresponding to the thickness range, and applying the selected gain value to an output signal from the first and second coils.

The logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

It will be appreciated that the above embodiments that have been described in particular detail are merely example or possible embodiments, and that there are many other combinations, additions, or alternatives that may be included.

Also, the particular naming of the components, capitalization of terms, the attributes, data structures, or any other programming or structural aspect is not mandatory or significant, and the mechanisms that implement the disclosure or its features may have different names, formats, or protocols. Further, the system may be implemented via a combination of hardware and software, as described, or entirely in hardware elements. Also, the particular division of functionality between the various system components described herein is merely one example, and not mandatory; functions performed by a single system component may instead be performed by multiple components, and functions performed by multiple components may instead performed by a single component.

Some portions of above description present features in terms of algorithms and symbolic representations of operations on information. These algorithmic descriptions and representations may be used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or "providing" or the like, refer to the action and processes of a computer system, or similar electronic computing device, that manipulates and transforms data represented as physical (electronic) quantities within the computer system memories or registers or other such information storage, transmission or display devices.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

As used herein, the term "computer" and related terms, e.g., "computing device", are not limited to integrated circuits referred to in the art as a computer, but broadly refers to a microcontroller, a microcomputer, a programmable logic controller (PLC), an application specific integrated circuit, and other programmable circuits, and these terms are used interchangeably herein.

As used herein, the term "mobile computing device" refers to any of computing device which is used in a portable manner including, without limitation, smart phones, personal digital assistants ("PDAs"), computer tablets, hybrid phone/computer tablets ("phablet"), or other similar mobile device capable of functioning in the systems described herein. In some examples, mobile computing devices may include a variety of peripherals and accessories including, without limitation, microphones, speakers, keyboards, touchscreens, gyroscopes, accelerometers, and metrological devices. Also, as used herein, "portable computing device" and "mobile computing device" may be used interchangeably.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

The term processor, as used herein, refers to central processing units, microprocessors, microcontrollers, reduced instruction set circuits (RISC), application specific integrated circuits (ASIC), logic circuits, and any other circuit or processor capable of executing the functions described herein.

As used herein, the terms "software" and "firmware" are interchangeable, and include any computer program stored in memory for execution by processors 104, 202, and/or 252 and by devices that include, without limitation, mobile devices, clusters, personal computers, workstations, clients, and servers, including RAM memory, ROM memory, EPROM memory, EEPROM memory, and non-volatile RAM (NVRAM) memory. The above memory types are examples only, and are thus not limiting as to the types of memory usable for storage of a computer program.

As will be appreciated based on the foregoing specification, the above-described embodiments of the disclosure may be implemented using computer programming or engineering techniques including computer software, firmware, hardware or any combination or subset thereof, the technical effect of the methods and systems may be achieved by performing at least one of the following steps: (a) providing calibration information to the eddy current device using the probe, (b) switching between a first mode and a second mode of the eddy current device, the first mode exciting only the first coil to measure liftoff of the probe from a surface of a workpiece, the second mode exciting the first and second coils to measure dimensions of a flaw within the workpiece, (c) determining a thickness of a non-conductive coating covering at least a portion of the workpiece using the first coil, (d) adjusting a gain setting of the eddy current device based on the determined thickness and the calibration information, and (e) determining dimensions of the flaw using the first and second coils and the adjusted gain setting. Any such resulting program, having computer-readable code means, may be embodied or provided within one or more computer-readable media, thereby making a computer program product, i.e., an article of manufacture, according to the discussed embodiments of the disclosure. The computer readable media may be, for example, but is not limited to, a fixed (hard) drive, diskette, optical disk, magnetic tape, semiconductor memory such as read-only memory (ROM), and/or any transmitting/receiving medium such as the Internet or other communication network or link. The article of manufacture containing the computer code may be made and/or used by executing the code directly from one medium, by copying the code from one medium to another medium, or by transmitting the code over a network.

Many of the functional units described in this specification have been labeled as modules, in order to more particularly emphasize their implementation independence. For example, a module may be implemented as a hardware circuit comprising custom very large scale integration ("VLSI") circuits or gate arrays, off-the-shelf semiconductors such as logic chips, transistors, or other discrete components. A module may also be implemented in programmable hardware devices such as field programmable gate arrays (FPGAs), programmable array logic, programmable logic devices (PLDs) or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

The above-described embodiments of a method and system of dynamically adjusting gain of an eddy current device provides a cost-effective and reliable means for accurate identification and measurement of detected flaws under changing conditions with minimal periodic recalibration. More specifically, the methods and systems described herein facilitate alternating modes of a measurement instrument to monitor measurement conditions for changes, to determine an appropriate correction, and to apply the correction at the next measurement period. As a result, the methods and systems described herein facilitate automatically maintaining accuracy of measurement devices under changing measurement conditions in a cost-effective and reliable manner.

This written description uses examples to describe the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A computer-implemented method for dynamically adjusting a gain of an eddy current device, the eddy current device communicatively coupled to a probe having at least a first coil and a second coil, the method implemented using a computer-controlled eddy current device coupled to a user interface and a memory device, the method comprising:
   providing calibration information to the eddy current device using the probe;
   switching between a first mode and a second mode of the eddy current device, the first mode exciting only the first coil to measure liftoff of the probe from a surface of a workpiece, the second mode exciting the first and second coils to measure dimensions of a flaw within the workpiece;
   determining a thickness of a non-conductive coating covering at least a portion of the workpiece using the first coil;
   adjusting a gain setting of the eddy current device based on the determined thickness and the calibration information; and
   determining dimensions of the flaw using the first and second coils and the adjusted gain setting.

2. The method of claim 1, wherein switching between a first mode and a second mode of the eddy current device comprises switching between a first mode and a second mode of the eddy current device at a frequency of greater than 0.1 Hertz (Hz).

3. The method of claim 1, wherein switching between a first mode and a second mode of the eddy current device comprises switching between a first mode and a second mode of the eddy current device at a frequency of greater than 5.0 kilohertz (kHz).

4. The method of claim 1, wherein adjusting a gain setting of the eddy current device based on the determined thickness and the calibration information comprises:
   comparing a current determined thickness to a thickness range of the calibration information;
   selecting a gain value of the calibration information corresponding to the thickness range; and
   applying the selected gain value to an output signal from the first and second coils.

5. An eddy current measuring system comprising:
   a processor coupled to a user interface and a memory device, the processor programmed to generate a plurality of multi-plexed eddy current probe excitation currents;
   a probe comprising at least a first coil and a second coil and configured to receive the excitation currents; and
   a dynamic gain adjustment circuit configured alternately to determine a gain signal relative to a thickness of a coating in contact with the probe using the first coil and to apply the gain signal to an output signal of the first and second coils.

6. The system of claim 5, wherein said eddy current measuring system is configured to generate calibration signals and receive calibration information using the probe.

7. The system of claim 5, wherein said processor is configured to switch the eddy current measuring system between a first mode and a second mode of the eddy current device at a rate selectable by a user.

8. The system of claim 5, wherein said eddy current measuring system comprises a first mode configured to excite only the first coil and a second mode configured to excite the first and second coils.

9. The system of claim 5, wherein said eddy current measuring system is configured to measure liftoff of the probe from a surface of a workpiece using the first coil.

10. The system of claim 5, wherein said eddy current measuring system is configured to determine a gain setting of the eddy current device based on the measured liftoff and the calibration information.

11. The system of claim 10, wherein said eddy current measuring system is configured to measure dimensions of a flaw within the workpiece using the first and second coils and the gain setting.

12. The system of claim 5, wherein said processor is configured to switch the eddy current measuring system between a first mode and a second mode at a rate greater than one Hertz (Hz).

13. The system of claim 5, wherein said processor is configured to switch the eddy current measuring system between a first mode and a second mode at a rate greater than one thousand Hertz (Hz).

14. The system of claim 5, wherein said processor is configured to switch the eddy current measuring system between a first mode and a second mode at a rate greater than fifty thousand Hertz (Hz).

15. One or more non-transitory computer-readable storage media having computer-executable instructions embodied thereon, wherein when executed by at least one processor of an eddy current device, the computer-executable instructions cause the at least one processor to:
receive calibration information using an eddy current probe communicatively coupled to the at least one processor;
switch between a first mode and a second mode of the eddy current device, the first mode exciting only a first coil of the eddy current probe to measure liftoff of the eddy current probe from a surface of a workpiece, the second mode exciting the first coil and a second coil to measure dimensions of a flaw within the workpiece;
determine a thickness of a non-conductive coating covering at least a portion of the workpiece using the first coil;
adjusting a gain setting of the eddy current device based on the determined thickness and the calibration information; and
determine dimensions of the flaw using the first and second coils and the adjusted gain setting.

16. The computer-readable storage media of claim 15, wherein the computer-executable instructions further cause the processor to generate calibration signals and receive calibration information using the probe.

17. The computer-readable storage media of claim 15, wherein the computer-executable instructions further cause the processor to switch the eddy current measuring system between a first mode and a second mode of the eddy current device at a rate selectable by a user.

18. The computer-readable storage media of claim 15, wherein the computer-executable instructions further cause the processor to measure liftoff of the probe from a surface of a workpiece using the first coil.

19. The computer-readable storage media of claim 15, wherein the computer-executable instructions further cause the processor to determine a gain setting of the eddy current device based on the measured liftoff and the calibration information.

20. The computer-readable storage media of claim 15, wherein the computer-executable instructions further cause the processor to measure dimensions of a flaw within the workpiece using the first and second coils and the gain setting.

* * * * *